United States Patent
Song et al.

(10) Patent No.: US 9,554,948 B2
(45) Date of Patent: Jan. 31, 2017

(54) ABSORBENT PRODUCTS WITH WETNESS SENSORS

(75) Inventors: Xuedong Song, Alpharetta, GA (US); Andrew M. Long, Appleton, WI (US); WanDuk Lee, Seoul (KR); Jun Mo Gil, Deajeon (KR)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 1469 days.

(21) Appl. No.: 12/491,701

(22) Filed: Jun. 25, 2009

(65) Prior Publication Data

US 2010/0030173 A1    Feb. 4, 2010

Related U.S. Application Data

(60) Provisional application No. 61/137,387, filed on Jul. 30, 2008.

(51) Int. Cl.
*A61F 13/15*    (2006.01)
*A61F 13/42*    (2006.01)

(52) U.S. Cl.
CPC ........ *A61F 13/42* (2013.01); *Y10T 428/24934* (2015.01); *Y10T 428/31993* (2015.04)

(58) Field of Classification Search
CPC ............... A61F 13/42; A61F 2013/421; A61F 2013/422; A61F 2013/425; A61F 2013/426; A61F 2013/427; A61F 2013/428; A61F 2013/429

USPC ................................................. 604/361, 367
See application file for complete search history.

(56) References Cited

U.S. PATENT DOCUMENTS

| | | | |
|---|---|---|---|
| 3,560,229 A | | 2/1971 | Farnham et al. |
| 5,197,958 A | * | 3/1993 | Howell ......................... 604/361 |
| 5,389,093 A | | 2/1995 | Howell |
| 2003/0045845 A1 | | 3/2003 | Yoshioka |
| 2007/0197986 A1 | | 8/2007 | Matsui |
| 2007/0270773 A1 | | 11/2007 | Mackey |
| 2011/0015063 A1 | | 1/2011 | Gil et al. |

FOREIGN PATENT DOCUMENTS

| EP | 0 611 661 A1 | 8/1994 |
|---|---|---|
| WO | WO 2005/035673 A1 | 4/2005 |
| WO | WO 2006/068723 A1 | 6/2006 |

* cited by examiner

*Primary Examiner* — Jacqueline Stephens
(74) *Attorney, Agent, or Firm* — Kimberly-Clark Worldwide, Inc.

(57) ABSTRACT

A sensor that is sensitive to the presence of aqueous-based fluids is described. The sensor has a wetness indicating material immobilized or printed on a substrate. The indicating material contains at least one electron-donating leuco dye and one electron deficient receptor, and exhibits a visual signal (e.g., vivid or strong color intensity) in a dry state, which fades or disappears when in contact with a water-containing liquid. An absorbent article incorporating such a sensor to communicate to a user that the article has been exposed to water-containing fluids is also described.

11 Claims, 6 Drawing Sheets

ABSORBENT PRODUCTS WITH WETNESS SENSORS

RELATED APPLICATION

Applicants hereby claim priority from presently U.S. Provisional Application No. 61/137,387 entitled "Absorbent Products with Wetness Sensors" and filed on Jul. 30, 2008, in the names of Xuedong Song, Andrew M. Long, WanDuk Lee, and JunMo Gil.

FIELD OF INVENTION

The present invention pertains to a sensor involving a visual color change due to the presence of an aqueous-based liquid. In particular, the invention relates to an absorbent article having a wetness indicator, with an electron-rich leuco dye and electron deficient receptor, that communicates to a caregiver or user that the article is ready for changing.

BACKGROUND

Wetness sensing capabilities in an absorbent article has been a desirable and welcome feature for a variety of modern hygiene products. Disposable absorbent articles such as diapers, training pants, incontinence pads, and the like are highly absorbent and efficiently pull moisture away from the wearer, reducing skin irritation caused by prolonged wetness exposure. However, because these articles are so absorbent, wearers may not realize they have urinated, particularly if they are inexperienced toddlers who may not recognize the meaning of body sensations associated with urination. Thus, the wearer may not recognize their urination control failure or be aware the article should be changed. Furthermore, parents or caregivers may no recognize that the absorbent article requires changing.

Visual mechanisms have also been employed to signal the presence of wetness in absorbent articles. There are a large number of wetness sensing technologies that currently exist including electronic-based wetness sensors, color-based wetness sensors, and enzyme-based wetness sensors. However, all those wetness sensing technologies are not ideal and have one or more limitations. For instance, the electronic based wetness sensors are generally too expensive to be disposable, while enzyme-based wetness sensors may have stability issues. Water-soluble dye-based wetness indicators often lack high detection sensitivity desirable for new-born diapers. They also provide poor color contrast which sometimes makes signal reading difficult.

Thus, a need exists for wetness sensors that are cheap, safe, easy to be implemented in absorbent products, and easy to read. An absorbent article that incorporates such a sensor would be particularly beneficial.

SUMMARY OF THE INVENTION

The present invention in accordance with one aspect pertains to an absorbent article with a wetness indicator or sensor for detecting the presence of water in an aqueous-containing media, such as bodily fluids or waste. The wetness sensor comprises a substrate and wetness indicating materials on the substrate. The substrate has at least one type of wetness indicating material immobilized or printed thereon and the indicating material contains at least one electron-donating leuco dye and one electron acceptive receptor. The indicating material on the substrate normally shows a strong color in its dry state. The strong color of the indicating materials become weak or disappear when in contact with water in a water-containing media such as mucus, urine, or fecal material (BM), which is insulted into the absorbent article.

In another embodiment of the present disclosure, an absorbent article with a wetness sensor for detecting the presence of a water-containing media for bodily fluids and waste, such as vaginal fluids, urine or low viscosity BM, is described. The wetness sensor consists of a substrate and wetness indicating materials on the substrate. The wetness indicating materials consist of at least three reagents: at least one electron-rich leuco dye, one electron-deficient acceptor and a wettability enhancing agent. As the substrate of the absorbent article becomes wet or moist, the strong color of the indicating materials begins to fade in proportion to the amount and contact with water. The greater the amount of water, the more rapidly the observable color of the indicating materials change.

In another embodiment of the present disclosure, a wetness sensor for detecting the presence of water in a water-containing media is described. The wetness sensor consists of at least a substrate and a wetness indicating material on the substrate. The wetness indicating material consists of at least two reagents: one electron-rich leuco dye and one electron-deficient acceptor.

In another embodiment of the present disclosure, a wetness sensor for detecting the presence of water in a water-containing media is described. The wetness sensor consists of at least a substrate and a wetness indicating material on the substrate. The wetness indicating material consists of at least three reagents: at least one electron-rich leuco dye, one electron-deficient acceptor and a wettability enhancing agent.

Alternatively, the present invention describes an absorbent article capable of determining the presence or absence of a water-containing liquid: a substantially liquid impermeable layer; a liquid permeable layer; an absorbent core positioned between the substantially liquid impermeable layer and the liquid permeable layer; and a sensor integrated into the article and positioned such that the sensor is in fluid communication with bodily fluids or waste provided by a wearer of the article. The sensor includes a substrate having at least one type of wetness indicating material immobilized or printed thereon and the indicating material contains at least one electron-donating leuco dye and one electron acceptive receptor. The electron donating leuco dye is one or a mixture of crystal violet lactone (blue); malachite green lactone (green); 1,3-dimethyl-6-diethylaminofluoran; 6-diethylamino-benzo[$\alpha$]-fluoran (red); 3-cyclohexyl methyl-amino-6-methyl-7-anilinofluoran (black); benzoyl leucomethylene blue (blue); ethyl leucomethylene blue (blue); methoxybenzoyl leucomethylene blue (blue); 2-(phenylimino ethanedilidene)-3,3-trimethyl-indoline (red); 1,3,3-trimethyl-indolino-7'-chloro-$\beta$-naphthospiropyran (purple); di-$\beta$-naphthospiropyran (purple); N-acetylauramine (yellow); N-phenylauramine (yellow); and rhodamine B lactam (red). The electron acceptive developing compound is selected from a group B consisting of zinc salicylate and bisphenol A.

The indicating material is coated over a surface of said substrate as either a) a monochromic color scheme alone, bi-chromic, or multiple colors, b) in various shapes and sizes, c) graphics of patterns or alpha numeric symbols and words, or combinations thereof. The color transition is from being either a) colored to uncolored, b) uncolored to colored, or c) a combination of a) and b). A cellulosic-based substrate, the substrate having at least one type of wetness indicating material immobilized or printed on a layer of said substrate; the indicating material contains at least one electron-donating leuco dye and one electron acceptive receptor; the indicating material of said sensor exhibits a color transition when contacting a water-containing liquid. The cellulosic-based substrate is a facial tissue or bath tissue, or a paper towel or wiper.

Other features and aspects of the present disclosure are discussed in greater detail below.

Repeat use of reference characters in the present specification and drawings is intended to represent same or analogous features or elements of the disclosure.

DETAILED DESCRIPTION OF THE INVENTION

Section I. —Definitions

Colored complexes formed between an electron-rich leuco dye and a electron deficient acceptor in a dry state are developed to generate inks of different colors.

Section II. —Description

In general, the present invention pertains to a sensor or indicator that can show either the presence or absence of an aqueous-based fluid or water-containing medium, such as vaginal fluid, or liquid and solid waste. In another aspect, the present invention also pertains to an absorbent article with such a wetness sensor for determining the presence or absence of water in a water-containing media. The sensor is made of at least a substrate and a wetness indicating material which is printed or immobilized on the substrate. The indicating material has at least one electron-donating leuco dye and an electron acceptor immobilized. The indicating material on the substrate gives an initial color or a pattern of one or more colors. The indicating material on the substrate normally shows a strong color in its dry state. The strong color of the indicating materials become weak or disappear when in contact with water in a water-containing media such as mucus, urine and/or fecal material (BM), which may insult the absorbent article to detect the presence or absence of the water-containing medium. In addition to the dye and acceptor, the sensor may also consist of other additives such as a wettability enhancing agent and/or a filler and/or surface tension modifier and/or a thickening agent and others.

The present invention addresses some of the problematic issues with current wetness indicators. In contrast to many existing wetness indication solutions that transform from colored to colorless when insulted with a liquid, the indicating materials in the present invention have more variety of colors and more sensitive. This signal in the indicator needs only a relatively small volume of liquid to manifest and is stable without leaching or diffusing in the presence of the liquid.

The present disclosure provides a relatively simple, compact and cost-efficient sensor for accurately detecting the presence or absence of urine. The test result can be visible so that it is readily observed by the person performing the test in a prompt manner and under test conditions conducive to highly reliable and consistent test results.

Figure 1A:
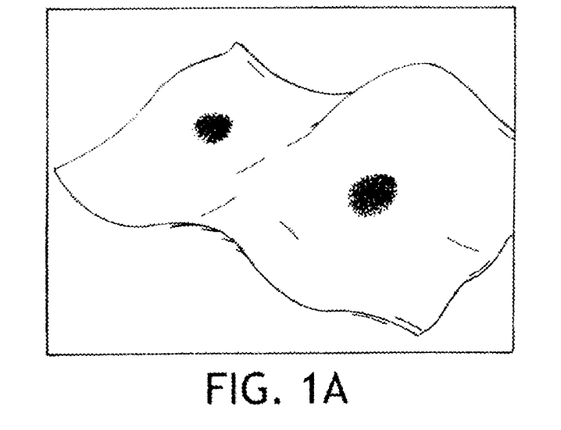
FIGS. 1A-1C are a series of schematic representations showing an indicator material (ink) applied to a polymer film layer according to an embodiment of a sensor according to the present invention, and the progressive fading of the indicator color intensity after contact with a water-containing fluid.
Figure 1B:
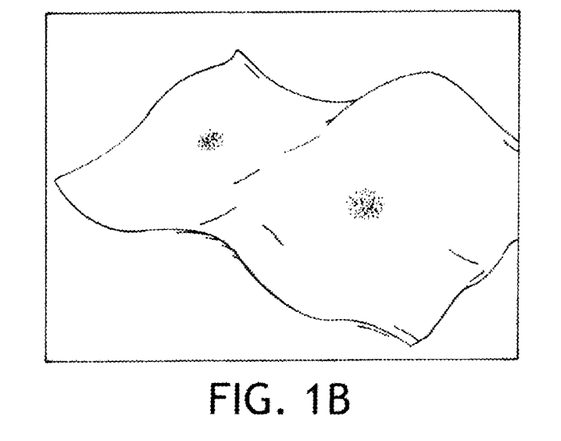
Figure 1C:
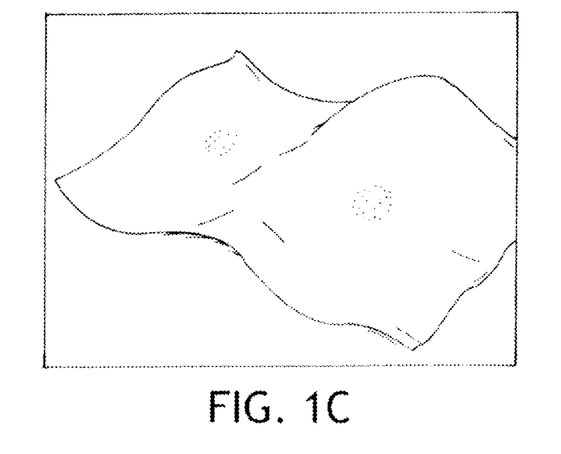

An illustration of an embodiment of the present sensor indicator material is presented in the series of schematic representations (photographs originally) shown in FIGS. 1A-1C. In FIG. 1A, the indicator material (blue ink) is deposited on a polymer film sheet and shows an initial strong color when dry (i.e., 0 μl urine). FIG. 1B shows changes in color intensity of the same indicator material after being exposed to about 200 μl of urine for two minutes. FIG. 1C shows the same indicator material as in FIG. 1B after being exposed to 200 μl of urine for 20 minutes. The color intensity of the blue ink fades with prolonged exposure to the urine. Even at a relatively small volume of liquid, over time, the indicator material is sensitive and communicates a visually observable signal.

Figure 2A:
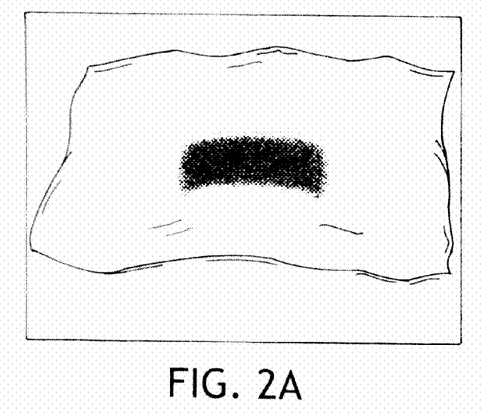
FIGS. 2A-2D are a series of schematic representations showing an indicator material (ink) applied to four cellulose-based substrates according to an embodiment of a sensor according to the present invention, and each respectively after contact with a different volume of water-containing fluid.
Figure 2B:
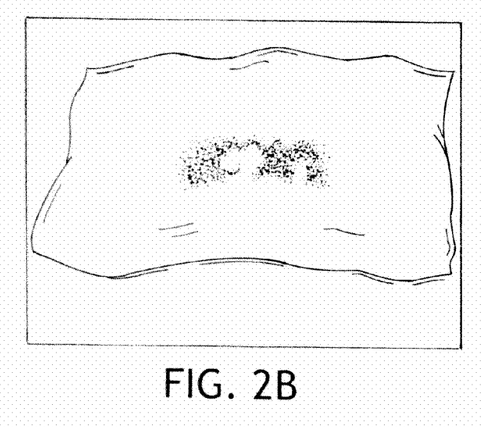
Figure 2C:
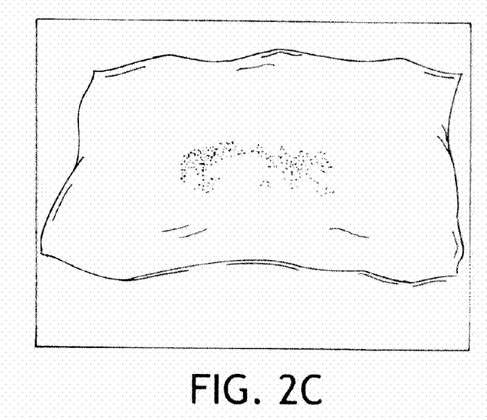
Figure 2D:
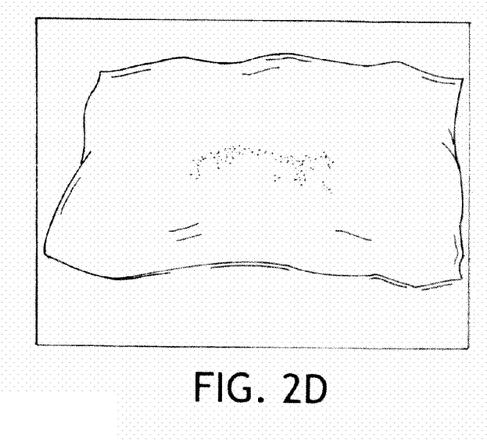

In another illustration, the indicator material (ink) is relatively quick to respond larger amounts of water-based fluid. FIG. 2A shows a fresh cellulose-based substrate, such as a facial tissue or a sheet made with fiber fluff, having a colored (blue) indicator material applied in a rectangular area. Each schematic drawing (photographs originally) of FIGS. 2B, 2C, and 2D, represents a fresh cellulosic substrate to which a different amount of a urine (respectively, about 5 ml, 10 ml, and 20 ml) has been applied near the center of the indicator colored rectangular area. Each photo was taken about two minutes after application of the urine. One can see that the color intensity of the indicator fades more dramatically with increasing fluid volume.

According to the invention, the indicator is made using a color ink agent that mixes at least one electron donating leuco dye and one electron acceptive developing compound and applying the ink to a substrate surface. The electron donative coloring compound is selected from a group A composed of crystal violet lactone (blue); malachite green lactone (green); 1,3-dimethyl-6-diethylaminofluoran; 6-diethylamino-benzo[α]-fluoran (red); 3-cyclohexyl methyl-amino-6-methyl-7-anilinofluoran (black); benzoyl leucomethylene blue (blue); ethyl leucomethylene blue (blue); methoxybenzoyl leucomethylene blue (blue); 2-(phenylimino ethanedilidene)-3,3-trimethyl-indoline (red); 1,3,3-trimethyl-indolino-7'-chloro-β-naphthospiropyran (purple); di-β-naphthospiropyran (purple); N-acetylauramine (yellow); N-phenylauramine (yellow); and rhodamine B lactam (red). The electron acceptlye developing compound is selected from a group B consisting of zinc salicylate and bisphenol A The specific details of the compounds in the ink formulation and its properties are described in U.S. Pat. No. 5,417,748, the content of which is incorporated herein by reference.

The ink can be applied generally over the entire substrate surface or at discrete localized spots on the substrate. The ink can be applied as a coating either in a monochromic color scheme alone, bi-chromic, or in multiple colors, or printed either in various shapes and sizes, graphics of patterns or alpha numeric symbols and/or words, or combinations thereof.

The useful substrates in the invention can vary. The substrates can be porous and hydrophobic films and sheet materials, or cellulosic-based substrates such as fiber fluff, paper tissues, paper sheets or towels and wipers. The substrates can also be nonporous plastic films and sheets, such as polyolefin films, or nonwoven materials. Examples of polyolefin films include polyethylene and polypropylene films, or modified polyethylene and polypropylene films. The substrates may be a part of an outer cover film of an absorbent article such as a diaper.

Depending on the particular nature of the substrate, the indicator composition would require addition of other ingredients to immobilize or make the color ink agent adhere to the substrate. In addition to the electron-rich leuco dye and electron deficient acceptor, the composition also may contain wettability enhancing agents such as surfactants and/or water-miscible or hydrophilic polymers, or water-soluble salts. Furthermore, the composition may also contain other additives to adjust viscosity, surface tension, or other physical and chemical properties. Alternatively, the substrates can be treated with different materials to modify their surface properties before the deposition of the composition to improve the adhesion of the composition. According to certain embodiments, a wettability enhancing agent is also applied in the color ink formulation. The wettability enhancing agent can be a surfactant or a mixture of surfactants. The surfactants can be non-ionic surfactants or ionic surfactants. The ionic surfactants can be either positively charged or negatively charged. The examples of non-ionic surfactants include alkyl poly(ethylene oxide) such as copolymers of poly(ethylene oxide) and poly(propylene oxide) (commercially called Poloxamers or Poloxamines), alkyl polyglucosides such as octyl glucoside and decyl maltoside, fatty alcohols such as cetyl alcohol, oleyl alcohol, cocamide MEA and cocamide DEA. The examples of ionic surfactants include anionic (e.g., based on sulfate, sulfonate or carboxylate anions) surfactants such as s (SDS), ammonium lauryl sulfate and other alkyl sulfate salts, Sodium laureth sulfate, also known as sodium lauryl ether sulfate (SLES), Alkyl benzene sulfonate, Soaps, or fatty acid salts; and Cationic (e.g., based on quaternary ammonium cations) surfactants such as Cetyl trimethylammonium bromide (CTAB) a.k.a. hexadecyl trimethyl ammonium bromide, and other alkyltrimethylammonium salts, Cetylpyridinium chloride (CPC), Polyethoxylated tallow amine (POEA), Benzalkonium chloride (BAC), Benzethonium chloride (BZT); or Zwitterionic (amphoteric) surfactants such as Dodecyl betaine, Dodecyl dimethylamine oxide, Cocamidopropyl betaine, Coco ampho glycinate. Alternatively, the wettability enhancing agents may also be hydrophilic molecules. The hydrophilic molecules may be small molecules such as sucrose, glucose and glycerol. The hydrophilic molecules may also be polymers such as polyethylene glycol and its copolymers.

A

In accordance with the present disclosure, one or more sensors described herein can also be integrated into an absorbent article. An "absorbent article" generally refers to any article capable of absorbing water or other fluids. Examples of some absorbent articles include, but are not limited to, personal care absorbent articles, such as diapers, training pants, absorbent underpants, incontinence articles, feminine hygiene products (e.g., sanitary napkins), swim wear, baby wipes, and so forth; medical absorbent articles, such as garments, fenestration materials, underzones, bedzones, bandages, absorbent drapes, and medical wipes; food service wipers; clothing articles; and so forth. Materials and processes suitable for forming such absorbent articles are well known to those skilled in the art. Typically, absorbent articles include a substantially liquid-impermeable layer (e.g., outer cover), a liquid-permeable layer (e.g., bodyside liner, surge layer, etc.), and an absorbent core.

A sensor for detecting the presence of an aqueous-based liquid that has a substrate with at least one type of wetness indicating material immobilized or printed on a layer of the substrate. The indicating material contains at least one electron-donating leuco dye and one electron acceptive receptor. As mentioned, the indicating material on the substrate normally shows a strong color in its dry state. The strong color of the indicating materials become weak or disappear when in contact with water-containing media. The water-containing liquid can be either bodily fluids or waste, such as mucus, urine or BM. The electron donating leuco dye is selected from a group A having at least one or a combination of crystal violet lactone (blue); malachite green lactone (green); 1,3-dimethyl-6-diethylaminofluoran; 6-diethylamino-benzo[α]-fluoran (red); 3-cyclohexyl methylamino-6-methyl-7-anilinofluoran (black); benzoyl leucomethylene blue (blue); ethyl leucomethylene blue (blue); methoxybenzoyl leucomethylene blue (blue); 2-(phenylimino ethanedilidene)-3,3-trimethyl-indoline (red); 1,3, 3-trimethyl-indolino-7'-chloro-β-naphthospiropyran (purple); di-β-naphthospiropyran (purple); N-acetylauramine (yellow); N-phenylauramine (yellow); and rhodamine B lactam (red). The electron acceptlye developing compound may be selected from a group B with zinc salicylate and bisphenol A.

The indicating material is on a layer of the substrate that is either on a top sheet of the substrate or within an undersheet that is visible to a caregiver. The indicating material further contains a wettability enhancing agent, or a hydrophilic water-soluble agent. The indicating material is applied either at discrete localized spots on the surface of said substrate or generally over the entire substrate surface. Alternatively, the indicating materials are printed in different patterns and shapes on the substrate. The substrate can be printed with multiple indicating materials on different portion of the substrate.

The wetness sensor may be composed of solid substrate on which is deposited with a colored chemical composition. The solid substrate can be any substrate that allows a deposition of the indicator composition to exhibit a color. The solid substrates may be porous or may not be porous. Examples of the solid substrate include, but not limited to, porous tissues, papers, polymeric films, metals, wood, plastics, rubbers, nonwoven materials and woven materials.

Typically, for consumer-related health and hygiene products, the sensor substrate can be made from a polyolefin, such as a plastic film consisting of polyethylene film and polypropylene film. The sensor substrate also can be made in part with cellulose-based sheets. According to an alternate embodiment for an absorbent product, such as feminine pads or tampons may contain one or more of the wetness sensors to show the insult of the absorbent product by menses or vaginal fluids. The sensors become colorless in the presence of a liquid sample containing a significant portion of water molecules (e.g., ≥80 µl or 90 µl). As stated before, the colored chemical composition has at lease one electron-rich leuco dye and one electron deficient acceptor. The wetness sensor becomes colorless upon contact with a liquid containing a sufficient amount of water (e.g., ≥100 µl or 200 µl).

B

Various embodiments of an absorbent article that can be formed according to the present disclosure will now be described in more detail. Only for purposes of further explaining the inventive concept, we will discuss an absorbent article in the embodiment of a diaper. A diaper can have an hourglass shape in an unfastened configuration. However, other shapes can of course be utilized, such as a generally rectangular shape, T-shape, or I-shape. The diaper may include a chassis formed by various components, including an outer cover, bodyside liner, absorbent core, and surge layer. It should be understood, however, that other layers can also be used in exemplary embodiments of the present disclosure. Likewise, one or more of the layers can also be eliminated in certain exemplary embodiments of the present disclosure.

Generally, the bodyside liner can be employed to help isolate the wearer's skin from liquids held in the absorbent core. For example, the liner presents a bodyfacing surface that is typically compliant, soft feeling, and non-irritating to the wearer's skin. Typically, the liner is also less hydrophilic than the absorbent core so that its surface remains relatively dry to the wearer. As indicated above, the liner can be liquid-permeable to permit liquid to readily penetrate through its thickness. Exemplary liner constructions that contain a nonwoven web are described in U.S. Pat. Nos. 5,192,606 to Proxmire, et al.; U.S. Pat. No.5,702,377 to Collier, I V, et al.; U.S. Pat. No. 5,931,823 to Stokes, et al.; U.S. Pat. No. 6,060,638 to Paul, et al.; and U.S. Pat. No. 6,150,002 to Varona, as well as U.S. Patent Application Publication Nos. 2004/0102750 to Jameson; 2005/0054255 to Morman, et al.; and 2005/0059941 to Baldwin, et al., all of which are incorporated herein in their entirety by reference thereto for all purposes.

The diaper can also include a surge layer that helps to decelerate and diffuse surges or gushes of liquid that can be rapidly introduced into the absorbent core. Desirably, the surge layer rapidly accepts and temporarily holds the liquid prior to releasing it into the storage or retention portions of the absorbent core. In the illustrated embodiment, for example, the surge layer is interposed between an inwardly facing surface of the bodyside liner and the absorbent core. Alternatively, the surge layer can be located on an outwardly facing surface of the bodyside liner. The surge layer typically can be constructed from highly liquid-permeable materials. Examples of suitable surge layers are described in U.S. Pat. No. 5,486,166 to Ellis, et al. and U.S. Pat. No. 5,490,846 to Ellis, et al., which are incorporated herein in their entirety by reference thereto for all purposes.

The outer cover typically can be formed from a material that is substantially impermeable to liquids. For example, the outer cover can be formed from a thin plastic film or other flexible liquid-impermeable material. In one embodiment, the outer cover is formed from a polyethylene film having a thickness of from about 0.01 millimeter to about 0.05 millimeter. The film can be impermeable to liquids, but permeable to gases and water vapor (i.e., "breathable"). This permits vapors to escape from the absorbent core, but still prevents liquid exudates from passing through the outer cover. If a more cloth-like feeling is desired, the outer cover can be formed from a polyolefin film laminated to a nonwoven web. For example, a stretch-thinned polypropylene film can be thermally laminated to a spunbond web of polypropylene fibers.

Besides the above-mentioned components, the diaper can also contain various other components as is known in the art. For example, the diaper can also contain a substantially hydrophilic tissue wrapsheet that helps maintain the integrity of the fibrous structure of the absorbent core. The tissue wrapsheet is typically placed about the absorbent core over at least the two major facing surfaces thereof, and composed of an absorbent cellulosic material, such as creped wadding or a high wet-strength tissue. The tissue wrapsheet can be configured to provide a wicking layer that helps to rapidly distribute liquid over the mass of absorbent fibers of the absorbent core. The wrapsheet material on one side of the absorbent fibrous mass can be bonded to the wrapsheet located on the opposite side of the fibrous mass to effectively entrap the absorbent core. Furthermore, the diaper can also include a ventilation layer (not shown) that is positioned between the absorbent core and the outer cover. When utilized, the ventilation layer can help insulate the outer cover from the absorbent core, thereby reducing dampness in the outer cover. Examples of such ventilation layers can include a nonwoven web laminated to a breathable film, such as described in U.S. Pat. No. 6,663,611 to Blaney, et al., which is incorporated herein in its entirety by reference thereto for all purposes.

In some embodiments, the diaper can also include a pair of side panels (or ears) that extend from the side edges of the diaper into one of the waist regions. The side panels can be integrally formed with a selected diaper component. For example, the side panels can be integrally formed with the outer cover or from the material employed to provide the top surface. In alternative configurations, the side panels can be provided by members connected and assembled to the outer cover, the top surface, between the outer cover and top surface, or in various other configurations. If desired, the side panels can be elasticized or otherwise rendered elastomeric by use of the elastic nonwoven composite of the present disclosure. Examples of absorbent articles that include elasticized side panels and selectively configured fastener tabs are described in PCT Patent Application WO 95/16425 to Roessler; U.S. Pat. No. 5,399,219 to Roessler et al.; U.S. Pat. No. 5,540,796 to Fries; and U.S. Pat. No. 5,595,618 to Fries, each of which is incorporated herein in its entirety by reference thereto for all purposes.

As representative of an absorbent article, the diaper can also include a pair of containment flaps that are configured to provide a barrier and to contain the lateral flow of body exudates. The containment flaps can be located along the laterally opposed side edges of the bodyside liner adjacent the side edges of the absorbent core. The containment flaps can extend longitudinally along the entire length of the absorbent core, or can only extend partially along the length of the absorbent core. When the containment flaps are shorter in length than the absorbent core, they can be selectively positioned anywhere along the side edges of diaper in a crotch region. In one embodiment, the containment flaps extend along the entire length of the absorbent core to better contain the body exudates. Such containment flaps are generally well known to those skilled in the art. For example, suitable constructions and arrangements for the containment flaps 112 are described in U.S. Pat. No. 4,704, 116 to Enloe, which is incorporated herein in its entirety by reference thereto for all purposes.

To provide improved fit and to help reduce leakage of body exudates, the diaper can be elasticized with suitable elastic members, as further explained below. For example, the diaper can include leg elastics constructed to operably tension the side margins of the diaper to provide elasticized leg bands which can closely fit around the legs of the wearer to reduce leakage and provide improved comfort and appearance. Waist elastics can also be employed to elasticize the end margins of the diaper to provide elasticized waistbands. The waist elastics are configured to provide a resilient, comfortably close fit around the waist of the wearer.

The diaper can also include one or more fasteners. For example, two flexible fasteners can be situated on opposite side edges of waist regions to create a waist opening and a pair of leg openings about the wearer. The shape of the fasteners can generally vary, but can include, for instance, generally rectangular shapes, square shapes, circular shapes, triangular shapes, oval shapes, linear shapes, and so forth. The fasteners can include, for instance, a hook-and-loop material, buttons, pins, snaps, adhesive tape fasteners, cohesives, fabric-and-loop fasteners, etc. In one particular embodiment, each fastener includes a separate piece of hook material affixed to the inside surface of a flexible backing.

The various regions and/or components of the diaper can be assembled together using any known attachment mechanism, such as adhesive, ultrasonic, thermal bonds, etc. Suitable adhesives can include, for instance, hot melt adhesives, pressure-sensitive adhesives, and so forth. When utilized, the adhesive can be applied as a uniform layer, a patterned layer, a sprayed pattern, or any of separate lines, swirls or dots. In the illustrated embodiment, for example, the outer cover and bodyside liner are assembled to each other and to the absorbent core using an adhesive. Alternatively, the absorbent core can be connected to the outer cover using conventional fasteners, such as buttons, hook and loop type fasteners, adhesive tape fasteners, and so forth. Similarly, other diaper components, such as the leg elastic members, waist elastic members and fasteners, can also be assembled into the diaper using any attachment mechanism.

Generally speaking, the sensors of the present disclosure can be incorporated into the absorbent article in a variety of different orientations and configurations, so long as the sensor is capable of receiving bodily fluids or waste (e.g., urine and/or fecal material) and providing a signal to a user or caregiver regarding the presence or absence of urine. The indicating materials containing the electron donating leuco dye and electron-deficient acceptors can directly be immobilized or printed on a portion of the inner side of the outer cover film of the article in different shapes and patterns. The indicating materials containing the electron donating leuco dye and electron-deficient acceptors can also be immobilized or printed on a piece of substrate to make a wetness sensor of different patterns which is sandwiched between the outer cover film and the superabsorbent materials of the article. Each portion of the patterns and shapes may be made of the indicating materials of different colors.

For example, sensor can be visible to the user or caregiver so that a simple, accurate, and rapid indication of wetness can be provided. The visibility can be accomplished in a variety of ways. For example, in some embodiments, the absorbent article can include a transparent or translucent portion (e.g., window, film, etc.) that allows the sensor to be readily viewed without removal of the absorbent article from the wearer and/or without disassembly of the absorbent article. In other embodiments, the sensor can extend through a hole or aperture in the absorbent article for observation. In still other embodiments, the sensor can simply be positioned on a surface of the absorbent article for observation.

Regardless of the particular manner in which it is integrated, urine can be directly discharged to a portion of the sensor, a liquid permeable cover or other material surrounding sensor, or can be discharged onto a component of the absorbent article into which the sensor has been integrated.

Reference now will be made in detail to various embodiments of the disclosure, one or more examples of which are set forth below. Each example is provided by way of explanation of the disclosure, not limitation of the disclosure. In fact, it will be apparent to those skilled in the art that various modifications and variations can be made in the present disclosure without departing from the scope or spirit of the disclosure. For instance, features illustrated or described as part of one embodiment, can be used on another embodiment to yield a still further embodiment. Thus, it is intended that the present disclosure covers such modifications and variations as come within the scope of the appended claims and their equivalents.

Figure 3:
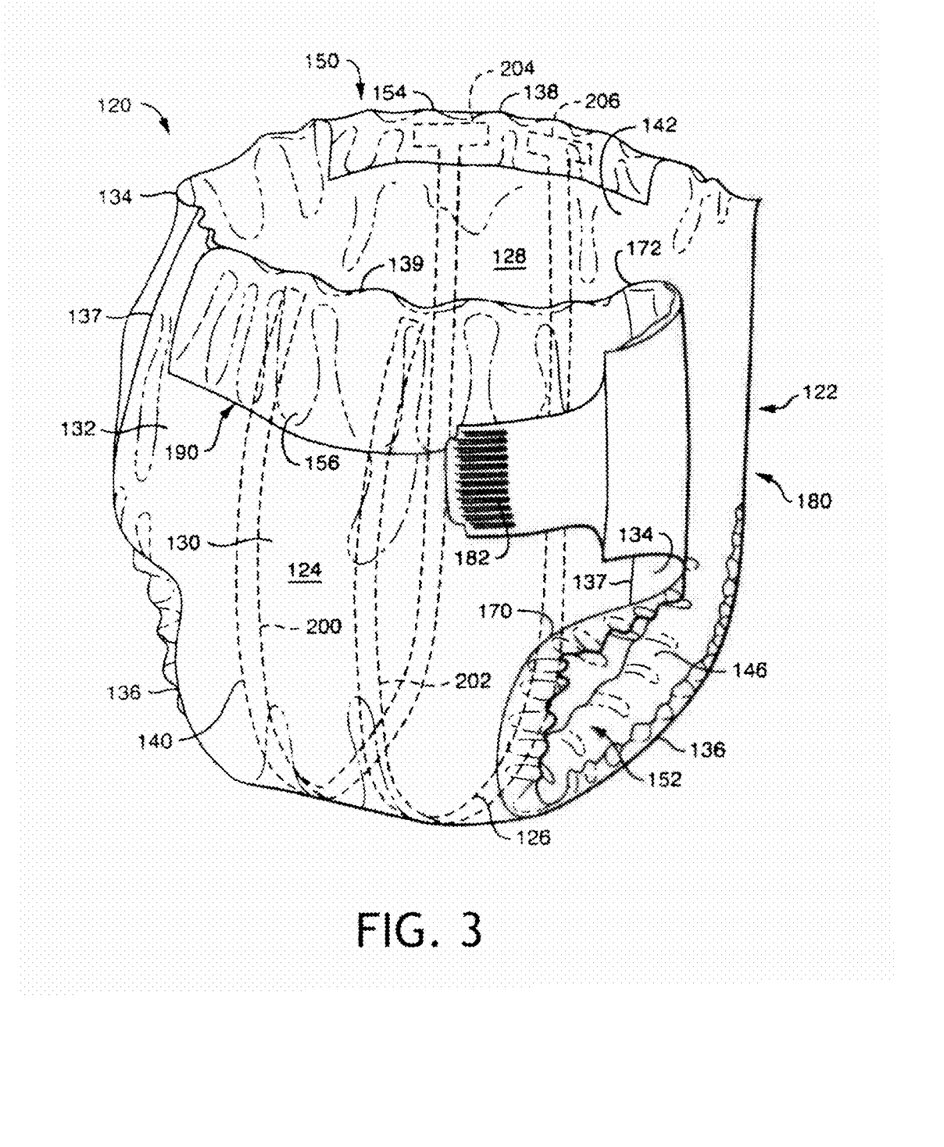
FIG. 3 is a rear perspective view of an embodiment of an absorbent article having one or more sensors according to FIG. 1 or 2.
Figure 4:
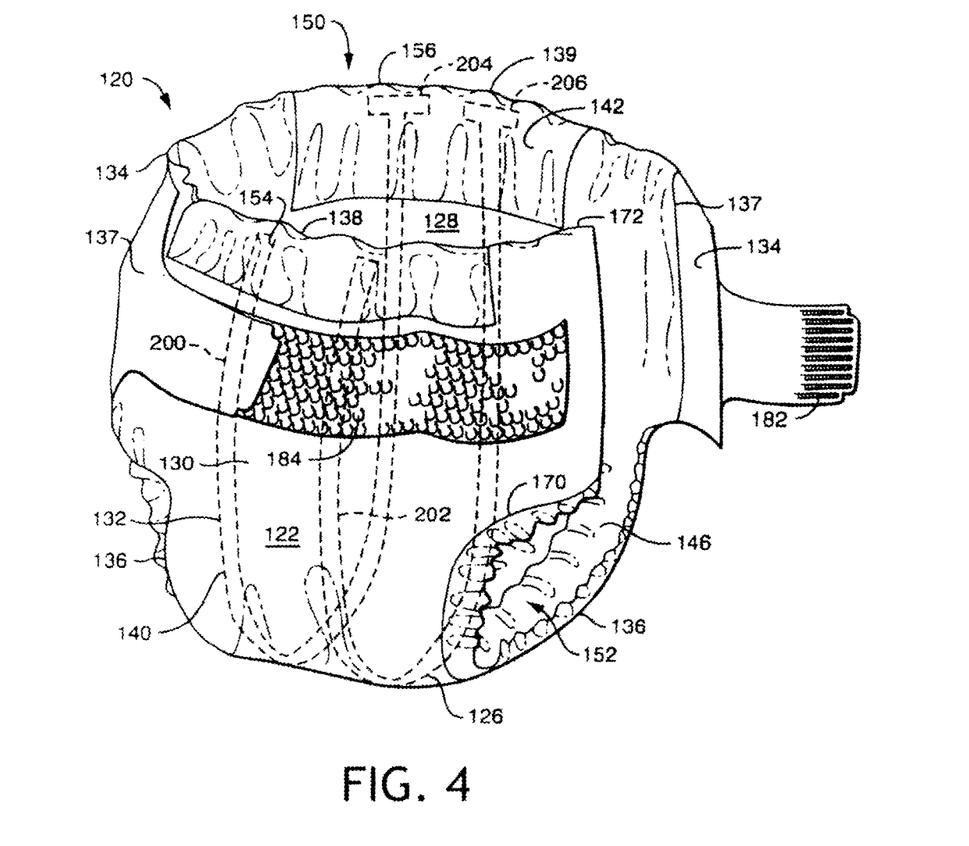
FIG. 4 is a front perspective view of the absorbent article shown in FIG. 3.

Referring to FIGS. 3 and 4, for exemplary purposes, an absorbent article 120 that may be made in accordance with the present disclosure is shown. The absorbent article 120 may or may not be disposable.

By way of illustration only, various materials and methods for constructing absorbent articles such as the diaper 120 of the various aspects of the present disclosure are disclosed in PCT Patent Application WO 00/37009 published Jun. 29, 2000 by A. Fletcher et al.; U.S. Pat. No. 4,940,464 issued Jul. 10, 1990 to Van Gompel et al.; U.S. Pat. No. 5,766,389 issued Jun. 16, 1998 to Brandon et al., and U.S. Pat. No. 6,645,190 issued Nov. 11, 2003 to Olson et al. which are incorporated herein by reference to the extent they are consistent (i.e., not in conflict) herewith.

Figure 5:
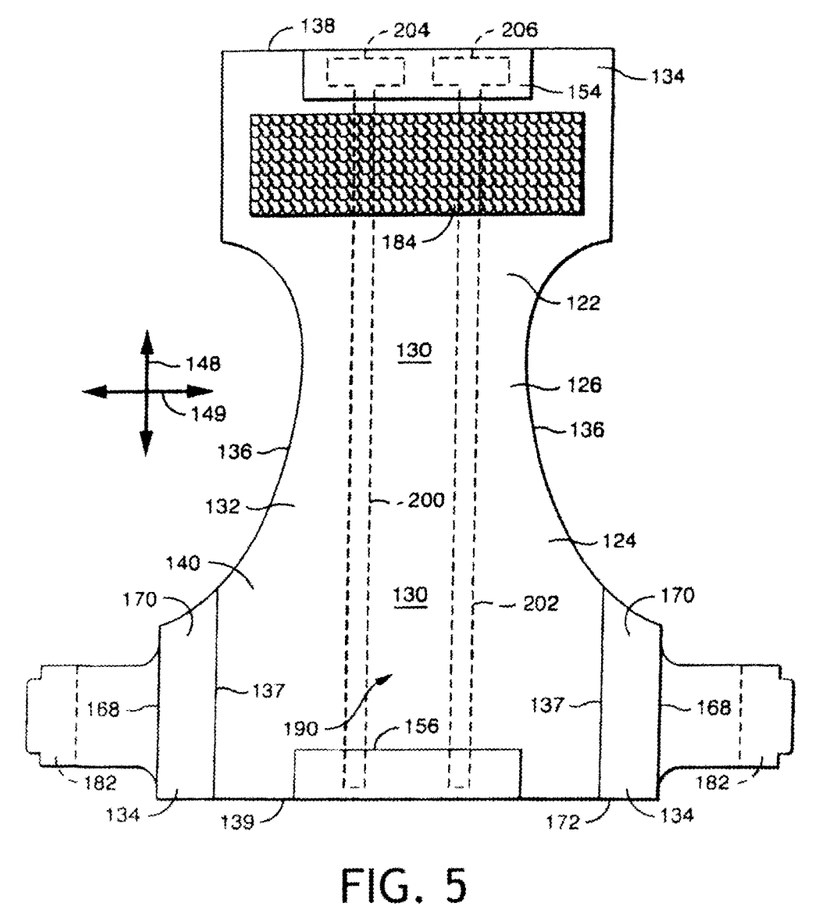
FIG. 5 is a plan view of the absorbent article of FIG. 3, as unfastened, unfolded, and laid out flat.
Figure 6:
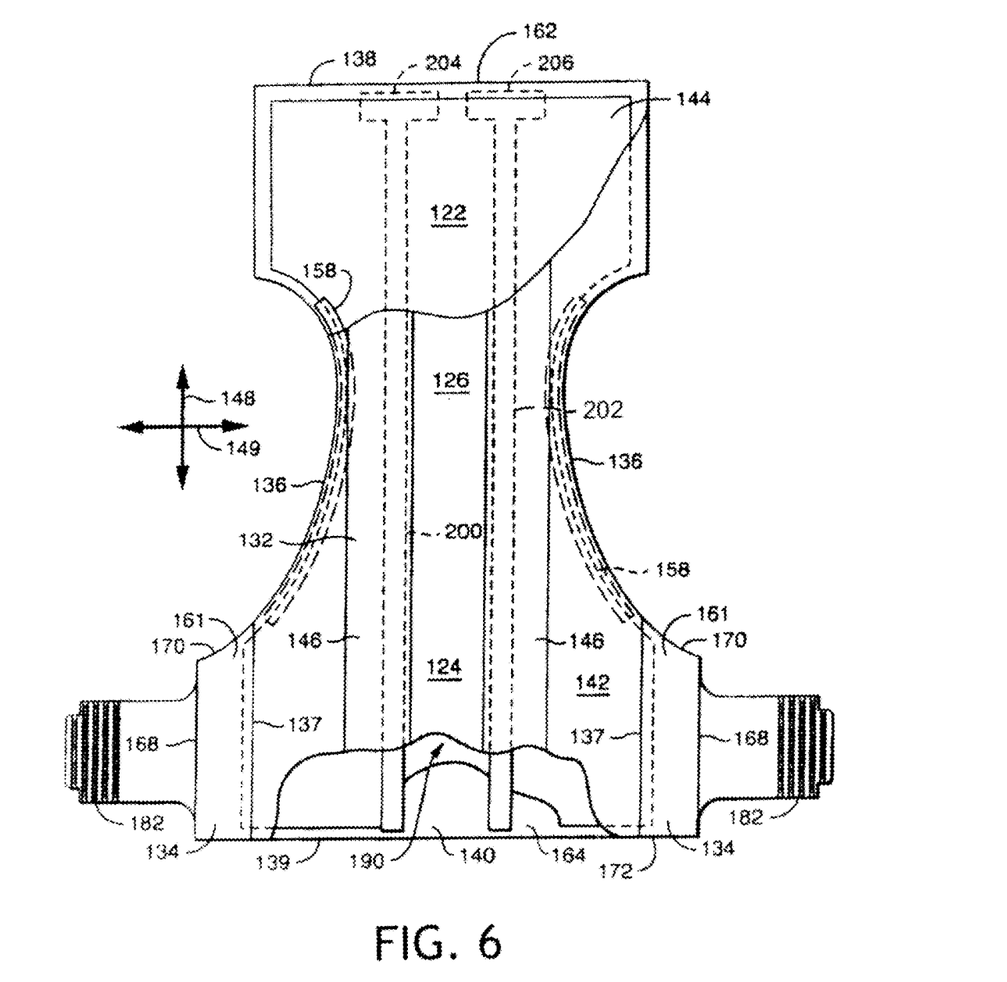
FIG. 6 is a plan view similar to FIG. 5, showing the surface of the absorbent article that faces the wearer when worn and with portions cut away to show underlying features.

A diaper 120 is representatively illustrated in FIG. 3 in a partially fastened condition. The diaper 120 shown in FIGS. 3 and 4 is also represented in FIGS. 5 and 6 in an opened and unfolded state. Specifically, FIG. 5 is a plan view illustrating the exterior side of the diaper 120, while FIG. 6 illustrates the interior side of the diaper 120. As shown in FIGS. 5 and 6, the diaper 120 defines a longitudinal direction 148 that extends from the front of the article when worn to the back of the article. Opposite to the longitudinal direction 148 is a lateral direction 149.

The diaper 120 defines a pair of longitudinal end regions, otherwise referred to herein as a front region 122 and a back region 124, and a center region, otherwise referred to herein as a crotch region 126, extending longitudinally between and interconnecting the front and back regions 122, 124. The diaper 120 also defines an inner surface 128 adapted in use (e.g., positioned relative to the other components of the article 120) to be disposed toward the wearer, and an outer surface 130 opposite the inner surface. The front and back regions 122, 124 are those portions of the diaper 120, which when worn, wholly or partially cover or encircle the waist or mid-lower torso of the wearer. The crotch region 126 generally is that portion of the diaper 120 which, when worn, is positioned between the legs of the wearer and covers the lower torso and crotch of the wearer. The absorbent article 120 has a pair of laterally opposite side edges 136 and a pair of longitudinally opposite waist edges, respectively designated front waist edge 138 and back waist edge 139.

The illustrated diaper 120 includes a chassis 132 that, in this aspect, encompasses the front region 122, the back region 124, and the crotch region 126. Referring to FIGS. 3-5, the chassis 132 includes an outer cover 140 and a bodyside liner 142 (FIGS. 3 and 6) that may be joined to the outer cover 140 in a superimposed relation therewith by adhesives, ultrasonic bonds, thermal bonds or other conventional techniques. Referring to FIG. 6, the liner 142 may suitably be joined to the outer cover 140 along the perimeter of the chassis 132 to form a front waist seam 162 and a back waist seam 164. As shown in FIG. 6, the liner 142 may suitably be joined to the outer cover 140 to form a pair of side seams 161 in the front region 122 and the back region 124. The liner 142 can be generally adapted, i.e., positioned relative to the other components of the article 120, to be disposed toward the wearer's skin during wear of the absorbent article. The chassis 132 may further include an absorbent structure 144 particularly shown in FIG. 6 disposed between the outer cover 140 and the bodyside liner 142 for absorbing liquid body exudates exuded by the wearer, and may further include a pair of containment flaps 146 secured to the bodyside liner 142 for inhibiting the lateral flow of body exudates.

The elasticized containment flaps 146 as shown in FIG. 6 define a partially unattached edge which assumes an upright configuration in at least the crotch region 126 of the diaper 120 to form a seal against the wearer's body. The containment flaps 146 can extend longitudinally along the entire length of the chassis 132 or may extend only partially along the length of the chassis. Suitable constructions and arrangements for the containment flaps 146 are generally well known to those skilled in the art and are described in U.S. Pat. No. 4,704,116 issued Nov. 3, 1987 to Enloe, which is incorporated herein by reference to the extent it is consistent (i.e., not in conflict) herewith.

To further enhance containment and/or absorption of body exudates, the diaper 120 may also suitably include leg elastic members 158 (FIG. 6), as are known to those skilled in the art. The leg elastic members 158 can be operatively joined to the outer cover 140 and/or the bodyside liner 142 and positioned in the crotch region 126 of the absorbent article 120.

The leg elastic members 158 can be formed of any suitable elastic material. As is well known to those skilled in the art, suitable elastic materials include sheets, strands or ribbons of natural rubber, synthetic rubber, or thermoplastic elastomeric polymers. The elastic materials can be stretched and adhered to a substrate, adhered to a gathered substrate, or adhered to a substrate and then elasticized or shrunk, for example with the application of heat, such that elastic retractive forces are imparted to the substrate. In one particular aspect, for example, the leg elastic members 158 may include a plurality of dry-spun coalesced multifilament spandex elastomeric threads sold under the trade name LYCRA and available from Invista, located at Wilmington, Del., U.S.A.

In some aspects, the absorbent article 120 may further include a surge management layer (not shown) which may be optionally located adjacent the absorbent structure 144 and attached to various components in the article 120 such as the absorbent structure 144 or the bodyside liner 142 by methods known in the art, such as by using an adhesive. A surge management layer helps to decelerate and diffuse surges or gushes of liquid that may be rapidly introduced into the absorbent structure of the article. Desirably, the surge management layer can rapidly accept and temporarily hold the liquid prior to releasing the liquid into the storage or retention portions of the absorbent structure. Examples of suitable surge management layers are described in U.S. Pat. No. 5,486,166, issued Jan. 23, 1996 to Bishop et al. and U.S. Pat. No. 5,490,846, issued Feb. 13, 1996 to Ellis et al. Other suitable surge management materials are described in U.S. Pat. No. 5,820,973, issued Oct. 13, 1998 to Dodge III et al. The entire disclosures of these patents are hereby incorporated by reference herein to the extent they are consistent (i.e., not in conflict) herewith.

As shown in FIGS. 3-6, the absorbent article 120 further includes a pair of opposing elastic side panels 134 that are attached to the back region of the chassis 132. As shown particularly in FIGS. 3 and 4, the side panels 134 may be stretched around the waist and/or hips of a wearer in order to secure the garment in place. As shown in FIGS. 5 and 6, the elastic side panels are attached to the chassis along a pair of opposing longitudinal edges 137. The side panels 134 may be attached or bonded to the chassis 132 using any suitable bonding technique. For instance, the side panels 134 may be joined to the chassis by adhesives, ultrasonic bonds, thermal bonds, or other conventional techniques.

In an alternative aspect, the elastic side panels may also be integrally formed with the chassis 132. For instance, the side panels 134 may include an extension of the bodyside liner 142, of the outer cover 140, or of both the bodyside liner 142 and the outer cover 140.

In the aspects shown in the figures, the side panels 134 are connected to the back region of the absorbent article 120 and extend over the front region of the article when securing the article in place on a user. It should be understood, however, that the side panels 134 may alternatively be connected to the front region of the article 120 and extend over the back region when the article is donned.

With the absorbent article 120 in the fastened position as partially illustrated in FIGS. 3 and 4, the elastic side panels 134 may be connected by a fastening system 180 to define a 3-dimensional diaper configuration having a waist opening 150 and a pair of leg openings 152. The waist opening 150 of the article 120 is defined by the waist edges 138 and 139 which encircle the waist of the wearer.

In the aspects shown in the figures, the side panels are releasably attachable to the front region 122 of the article 120 by the fastening system. It should be understood, however, that in other aspects the side panels 134 may be permanently joined to the chassis 132 at each end. The side panels 134 may be permanently bonded together, for instance, when forming a training pant or absorbent swimwear.

The elastic side panels 134 each have a longitudinal outer edge 168, a leg end edge 170 disposed toward the longitudinal center of the diaper 120, and waist end edges 172 disposed toward a longitudinal end of the absorbent article. The leg end edges 170 of the absorbent article 120 may be suitably curved and/or angled relative to the lateral direction 149 to provide a better fit around the wearer's legs. However, it is understood that only one of the leg end edges 170 may be curved or angled, such as the leg end edge of the back region 124, or alternatively, neither of the leg end edges may be curved or angled, without departing from the scope of the present disclosure. As shown in FIG. 6, the outer edges 168 are generally parallel to the longitudinal direction 148 while the waist end edges 172 are generally parallel to the transverse axis 149. It should be understood, however, that in other aspects the outer edges 168 and/or the waist edges 172 may be slanted or curved as desired. Ultimately, the side panels 134 are generally aligned with a waist region 190 of the chassis.

The fastening system 180 may include laterally opposite first fastening components 182 adapted for refastenable engagement to corresponding second fastening components 184. In the aspect shown in the figures, the first fastening component 182 is located on the elastic side panels 134, while the second fastening component 184 is located on the front region 122 of the chassis 132. In one aspect, a front or outer surface of each of the fastening components 182, 184 includes a plurality of engaging elements. The engaging elements of the first fastening components 182 are adapted to repeatedly engage and disengage corresponding engaging elements of the second fastening components 184 to releasably secure the article 120 in its three-dimensional configuration.

The fastening components 182, 184 may be any refastenable fasteners suitable for absorbent articles, such as adhesive fasteners, cohesive fasteners, mechanical fasteners, or the like. In particular aspects the fastening components include mechanical fastening elements for improved performance. Suitable mechanical fastening elements can be provided by interlocking geometric shaped materials, such as hooks, loops, bulbs, mushrooms, arrowheads, balls on stems, male and female mating components, buckles, snaps, or the like.

In the illustrated aspect, the first fastening components 182 include hook fasteners and the second fastening components 184 include complementary loop fasteners. Alternatively, the first fastening components 182 may include loop fasteners and the second fastening components 184 may be complementary hook fasteners. In another aspect, the fastening components 182, 184 can be interlocking similar surface fasteners, or adhesive and cohesive fastening elements such as an adhesive fastener and an adhesive-receptive landing zone or material, or the like. One skilled in the art will recognize that the shape, density and polymer composition of the hooks and loops may be selected to obtain the desired level of engagement between the fastening components 182, 184. Suitable fastening systems are also disclosed in the previously incorporated PCT Patent Application WO 00/37009 published Jun. 29, 2000 by A. Fletcher et al. and the previously incorporated U.S. Pat. No. 6,645,190 issued Nov. 11, 2003 to Olson et al.

In the aspect shown in the figures, the fastening components 182 are attached to the side panels 134 along the edges 168. In this aspect, the fastening components 182 are not elastic or extendable. In other aspects, however, the fastening components may be integral with the side panels 134. For example, the fastening components may be directly attached to the side panels 134 on a surface thereof.

In addition to possibly having elastic side panels, the absorbent article 120 may include various waist elastic members for providing elasticity around the waist opening. For example, as shown in the figures, the absorbent article 120 can include a front waist elastic member 154 and/or a back waist elastic member 156.

Section III —Examples

The present disclosure can be better understood with reference to the following empirical examples:

Example

1. A blue colored ink having an electron donative component and an electron acceptive developing component (PapyEco Ltd. Co., Japan) is applied to a piece or portion of the kinds of following substrates: a) cellulosic paper, such as Kimwipes or Kleenex® brand facial tissue (e.g., illustrated in FIGS. 2A-2D), and b) polymeric films, plastics and polyolefins, such as the outer cover film of a diaper and spun-bond non-woven materials (e.g., illustrated in FIGS. 1A-1C—blue ink alone on film). The ink materials are allowed to air-dry at room temperature. A piece of each of the above kind of materials is sandwiched between the superabsorbant material and the outer cover using a tape to secure the pieces. Different amounts of urine are applied to the center of the diaper. For wetness sensor with cellulosic papers, such as Kimwipes, 5 ml of urine causes little discoloration after 5 minutes. Significant discoloration is observed 5 minutes after 10 ml urine insult. Most of the color disappears about 5 minutes after 20 ml urine insults. For the wetness indicator using a Kleenex-brand facial tissue substrate, similar results are obtained as the indicator on Kimwipes. For the wetness indicator on the outer cover film of the diaper material, the visible discoloration typically occurs after at least about 20 minutes. The degree of discoloration is not as deep as the wetness indicators on porous cellulosic tissues. For the wetness indicator on a spun-bond nonwoven material, only slight discoloration is observed about 20 minutes after 20 ml urine insult. Strong color signal remains even at 1 hour after 20 ml urine insult.

2. A control wetness indicating solution is made using about 25 mg of crystal violet lactone and 50 mg of salicylate dissolved in 20 ml ethanol. Another wetness indicating solution is made using about 25 mg of crystal violet lactone, 50 mg of salicylate and 10 µl of Tween 40 (40% in water) dissolved in ethanol. The solutions are separately applied to a piece of outer cover film of a diaper and were air-dried. A 200 µl sample of urine is applied to each of the wetness indication materials, above, as in Example 1. The color on the wetness indicating material with Tween 40 disappeared almost completely about 5 minutes after sample was applied. In contrast, the color disappears only after about 20 minutes for the wetness materials without Tween 40. This is a significant difference in the persistence of the solution.

3. A piece of the wetness indicator in Example 2 along with the control indicator is sandwiched in parallel between the outer cover and the superabsorbant core of a diaper. About 10 ml of urine is added to the diaper in the center of the inner side. The discoloration for the indictor with Tween 40 is more than three times faster than the control indicator without Tween 40 upon insults of 20 ml synthetic urine.

4. The cellulosic papers (e.g., Kimwipes or Kleenex-brand tissues) change to blue when the control ink is applied and dried. The blue color remained stable for up to at least about 7 days (150-180 hours). In contrast, the blue color became colorless for the ink with Tween 40 to be applied on those cellulose based porous substrates over a couple of days.

5. Wetness indicating solution I contains 25 mg of crystal violet lactone and 50 mg of salicylate dissolved in 20 ml ethanol. Wetness indicating solution II contains 25 mg of crystal violet lactone, 50 mg of salicylate and 10 µl of Tween 40 (40% in water) dissolved in ethanol. The ink solutions were separately applied to the inner side of the outer cover film of a diaper and air-dried. The outer cover film is then secured against the superabsorbent core of the diaper using cellaphane tape. Insults of 20 ml synthetic urine cause the discoloration of the blue colors formed from both solutions within 10 minutes. However, the discoloration is very slow and not complete when the indicating solution without Tween 40 was applied to the outer cover films of a Kimberly-Clark's Huggies®-brand diaper and a Procter & Gamble's Pampers®-brand diaper.

6. A wetness indicating solution containing about 25 mg of crystal violet lactone and 50 mg of salicylate dissolved in 20 ml ethanol is used as a control. Another 25 mg of crystal violet lactone, 50 mg of salicylate and 10 ul of Tween 40 (40% in water) dissolved in ethanol is used to make an empirical wetness indicating solution. The two solutions are applied to a piece of a plastic zip-lock bag and was air-dried to show blue color. A 50 µl sample of urine is applied to the wetness indication material on the plastic bag and the blue color disappears almost immediately. A piece of the plastic bag was used to replace a piece of the outer cover film of a diaper and was secured against the superabsorbent materials. Insult of 20 ml synthetic urine into the diaper causes a portion of the blue color to colorless.

7. As in Example 1, a blue colored ink from PapyEco Ltd. Co. is applied to a piece of the following substrates: cellulosic tissues (e.g., Kimwipes, Kleenex-brand facial tissue), and polymeric films and polypropylene (e.g., outer cover film of a diaper and spun-bond non-woven materials). The materials were allowed to air-dry at room temperature. A piece of each of the above materials is sandwiched between the superabsorbant material and the outer cover using a tape to secure the pieces. Different amounts of urine are applied to the center of the diaper. For wetness sensor with Kimwipes, 5 ml of urine causes little discoloration after 5 minutes. Significant discoloration was observed 5 minutes after 10 ml urine insult. Most of color disappeared 5 minutes after 20 ml urine insults. For the wetness indicator with Kleenex facial tissue, similar results were obtained to the indicator on Kimwipes. For the wetness indicator on the outer cover film of a diaper, the visible discoloration normally took at least 20 minutes. The degree of discoloration is normally not as deep as the wetness indicators on porous tissues. For the wetness indicator on the spun-bond nonwoven material, only slight discoloration was observed 20 minutes after 20 ml urine insult. Strong color still remained even 1 hour after 20 ml urine insult.

8. An amount of about 25 mg of crystal violet lactone and 50 mg of salicylate are dissolved in 20 ml ethanol to make a control wetness indicating solution. Another 25 mg of crystal violet lactone, 50 mg of salicylate and 10 µl of Tween 40 (40% in water) are dissolved in ethanol to make a wetness indicating solution. The two solutions were separately applied to a piece of outer cover film of a diaper and air-dried. A 200 µl sample of urine is applied to each wetness indicating material. The color on the wetness indicating material that contained Tween 40 disappeared almost completely at about 5 minutes after sample application; while, in contrast, it can take up to about 20 minutes for the color to disappear for the wetness materials without Tween 40.

9. A piece of the wetness indicator in Example 2 along with the control indicator was sandwiched in parallel between the outer cover and the superabsorbant core of a diaper. A 10 ml sample of urine is added to the diaper in the center of the inner side. The discoloration for the indictor with Tween 40 is more than three times faster than the control indicator without Tween 40 upon insults of 20 ml synthetic urine.

10. The cellulosic papers (e.g., Kimwipes or Kleenex-branded tissues) became blue when the control ink is applied and dried. The blue color remained stable for up to about a week (150-180 hours). In contrast, the blue color faded or disappeared over a couple of days (48-60 or 72 hours) to become colorless for the ink with Tween 40 to be applied on the cellulose based porous substrates.

11. An amount of about 25 mg of crystal violet lactone and 50 mg of salicylate is dissolved in 20 ml ethanol to make a wetness indicating solution I. About 25 mg of crystal violet lactone, 50 mg of salicylate and 10 µl of Tween 40 (40% in water) were dissolved in ethanol to make a wetness indicating solution II. The ink solutions were separately applied to the inner side of the outer cover film of a diaper and were air-dried. The outer cover film was then secured against the superabsorbent core of the diaper using clear cellaphane tapes. Insults of 20 ml synthetic urine cause the discoloration of the blue colors formed from both solutions within 10 minutes. However, the discoloration is very slow and not complete when the indicating solution without Tween 40 was applied to the outer cover films of Huggies®-brand diapers by Kimberly-Clark Corporation and Pampers®-brand diapers by Procter & Gamble.

12. An amount of about 25 mg of crystal violet lactone and 50 mg of salicylate were dissolved in 20 ml ethanol to make a control wetness indicating solution. Using 25 mg of crystal violet lactone, 50 mg of salicylate and 10 µl of Tween 40 (40% in water) dissolved in ethanol to make a wetness indicating solution, the solution is applied to a piece of a[plastic zip-lock bag and was air-dried to show blue color. A 50 µl sample of urine is applied to the wetness indication material on the zip-lock bag and the blue color disappears almost immediately. A piece of the zip-lock bag is used to replace a piece of the outer cover film of a diaper and is secured against the superabsorbent materials. Insult of 20 ml synthetic urine into the diaper causes a portion of the blue color to colorless.

13. Examples of potential acceptive receptors: benzoic acid, p-tert-butylbenzoic acid, trichlorobenzoic acid, terephthalic acid, 3-sec-butyl-4-hydroxybenzoic acid, 3-cyclohexyl-4-hydroxybenzoic acid, 3,5-dimethyl-4-hydroxybenzoic acid, salicylic acid, 3-isopropylsalicylic acid, 3-tert-butylsalicylic acid, 3-benzylsalicylic acid, 3-($\alpha$-methylbenzyl) salicylic acid, 3-chloro-5-($\alpha$-methylbenzyl)salicylic acid, 3,5-di-tert-butylsalicylic acid, 3-phenyl-5-($\alpha,\alpha$-dimethylbenzyl) salicylic acid, 3,5-di($\alpha$-methylbenzyl)salicylic acid and like aromatic carboxylic acids; salts of these aromatic carboxylic acids with polyvalent metals such as zinc, magnesium, aluminum, calcium, titanium, manganese, tin, nickel or the like organic acidic substances.

14. Examples of penetration enhancing agents: sodium polyoxyethylenealkyl ether sulfate, triethanolamine polyoxyethylenealkyl ether sulfate, sodium polyoxyethylenealkyl phenyl ether sulfate or the like; nonionic surfactants such as polyoxyethylene lauryl ether, polyoxyethylene oleyl ether, polyoxyethylene nonyl phenyl ether, polyoxyethylene sorbitan monolaurate, polyethylene glycol monostearate 15. Examples of binders: hydroxyethyl cellulose; methyl cellulose; ethyl cellulose; carboxymethyl cellulose; gelatin; casein; gum arabic; water-soluble polymers such as polyvinyl alcohol and styrene-maleic anhydride copolymer salt; water-dispersible polymers either in the form of latex or emulsion such as styrene-butadiene copolymer latex, acrylic acid ester polymer emulsion, polyvinyl acetate latex, polyvinyl chloride latex; polymers soluble in an organic solvent such as polyvinylbutyral, polyvinyl acetate, vinyl chloride-vinyl acetate copolymer, acrylic resin, styrene resin, polyester resin 16. Experiments using a binder and penetration enhancing agent: A control wetness indicating solution is made using about 25 mg of crystal violet lactone, 250 mg of dimethylphthalate and 50 mg of salicylate dissolved in 20 ml ethanol. Another wetness indicating solution is made using about 25 mg of crystal violet lactone, 50 mg of salicylate, 250 mg of dimethylphthalate and 10 μl of Tween 40 (40% in water) dissolved in ethanol. The solutions are separately applied to a piece of outer cover film of a diaper and were air-dried. A 200 μl sample of urine is applied to each of the wetness indication materials, above, as in Example 1. The color on the wetness indicating material with Tween 40 disappeared almost completely about 5 minutes after sample was applied. In contrast, the color disappears only after about 20 minutes for the wetness materials without Tween 40.

The present invention has been described in general and in detail by means of examples. Persons of skill in the art understand that the invention is not limited necessarily to the embodiments specifically disclosed, but that modifications and variations may be made without departing from the scope of the invention as defined by the following claims or their equivalents, including other equivalent components presently known, or to be developed, which may be used within the scope of the present invention. Therefore, unless changes otherwise depart from the scope of the invention, the changes should be construed as being included herein.

We claim:

1. An absorbent article capable of determining the presence or absence of a water-containing liquid, the absorbent article comprising:
    a chassis comprised of a substantially liquid impermeable outercover and a liquid permeable bodyside liner, the chassis having a front waist seam, a back waist seam and a pair of opposing side seams; wherein the bodyside liner is attached to the outercover at the front waist seam, the back waist seam and the pair of opposing side seams; and
    an absorbent core positioned between the substantially liquid impermeable outercover and the liquid permeable bodyside liner; and
    a sensor integrated into the article and positioned such that the sensor is in fluid communication with bodily fluids or waste from a wearer of the article,
    the sensor comprising a substrate, the substrate having at least one type of wetness indicating material immobilized or printed thereon, wherein and the indicating material contains at least one electron-donating leuco dye and one electron deficient receptor, and wherein the indicating material contains a wettability enhancing agent or a hydrophilic water-soluble agent;
    wherein the sensor is capable of a color transition from a color to a weaker color or colorless when in contact with said bodily fluid or waste.

2. The absorbent article according to claim 1, wherein the substrate is made from a polyolefin.

3. The absorbent article according to claim 2, wherein the substrate is a plastic film consisting of polyethylene film and polypropylene film.

4. The absorbent article according to claim 1, wherein said substrate is in part a cellulose-based sheet.

5. The absorbent article according to claim 1, wherein the indicating material is applied either at discrete localized spots on the surface of said substrate or generally over the entire substrate surface.

6. The absorbent article according to claim 1, wherein the indicating materials are printed in different patterns and shapes on the substrate.

7. The absorbent article according to claim 1, wherein the substrate is printed with multiple indicating materials on different portion of the substrate.

8. The absorbent article according to claim 1, wherein said electron donating leuco dye is one or a mixture of crystal violet lactone (blue); malachite green lactone (green); 1,3-dimethyl-6-diethylaminofluoran; 6-diethylamino-benzo[α]-fluoran (red); 3-cyclohexyl methylamino-6-methyl-7-anilinofluoran (black); benzoyl leucomethylene blue (blue); ethyl leucomethylene blue (blue); methoxybenzoyl leucomethylene blue (blue); 2-(phenylimino ethanedilidene)-3,3-trimethyl-indoline (red); 1,3,3-trimethyl-indolino-7'-chloro-β-naphthospiropyran (purple); di-β-naphthospiropyran (purple); N-acetylauramine (yellow); N-phenylauramine (yellow); and rhodamine B lactam (red).

9. The absorbent article according to claim 1, wherein the electron deficient receptor is selected from a group B consisting of zinc salicylate.

10. The absorbent article according to claim 1, wherein said indicating material is coated over a surface of said substrate as either a) a monochromic color scheme alone, bi-chromic, or multiple colors, b) in various shapes and sizes, c) graphics of patterns or alpha numeric symbols and words, or combinations thereof.

11. An absorbent article capable of determining the presence or absence of a water-containing liquid, the absorbent article comprising:
    a chassis comprised of a substantially liquid impermeable outercover and a liquid permeable bodyside liner, the chassis having a front waist seam, a back waist seam and a pair of opposing side seams; wherein the bodyside liner is attached to the outercover at the front waist seam, the back waist seam and the pair of opposing side seams; and
    an absorbent core positioned between the substantially liquid impermeable outercover and the liquid permeable bodyside liner; and
    a sensor integrated into the article and positioned such that the sensor is in fluid communication with bodily fluids or waste from a wearer of the article,
    the sensor comprising a substrate, the substrate having at least one type of wetness indicating material immobilized or printed thereon, wherein and the indicating material contains at least one electron-donating leuco dye and one electron deficient receptor;
    wherein the sensor is capable of a color transition from a color to a weaker color or colorless when in contact with said bodily fluid or waste.

\* \* \* \* \*